US00PP26262P2

(12) United States Plant Patent
Heemskerk

(10) Patent No.: US PP26,262 P2
(45) Date of Patent: Dec. 22, 2015

(54) ***ZAMIOCULCAS* PLANT NAMED 'HEEMZAMIO'**

(50) Latin Name: *Zamioculcas zamiifolia*
Varietal Denomination: Heemzamio

(71) Applicant: Harold Heemskerk, De Kwakel (NL)

(72) Inventor: Harold Heemskerk, De Kwakel (NL)

(73) Assignee: KWEKERIJ HAROLD HEEMSKERK B.V., De Kwakel (NL)

( * ) Notice: Subject to any disclaimer, the term of this patent is extended or adjusted under 35 U.S.C. 154(b) by 90 days.

(21) Appl. No.: 13/999,235

(22) Filed: Jan. 31, 2014

(51) Int. Cl.
*A01H 5/12* (2006.01)

(52) U.S. Cl.
USPC ..... Plt./373

(58) Field of Classification Search
USPC ..... Plt./263.1, 373
See application file for complete search history.

*Primary Examiner* — Susan McCormick Ewoldt
(74) *Attorney, Agent, or Firm* — C. A. Whealy

(57) ABSTRACT

A new and distinct cultivar of *Zamioculcas* plant named 'Heemzamio', characterized by its upright plant habit with upwardly pointing pinnately-compound leaves; basally clumping habit; moderately vigorous growth habit; glossy leaflets that are dark greyed green and purple in color and at a distance, appear almost black in color; and glossy and cylindrical leaf rachises that are dark greyed green in color.

1 Drawing Sheet

Botanical designation: *Zamioculcas zamiifolia.*
Cultivar denomination: 'HEEMZAMIO'.

BACKGROUND OF THE INVENTION

The present invention relates to a new and distinct cultivar of *Zamioculcas* plant, botanically known as *Zamioculcas zamiifolia* and hereinafter referred to by the name 'Heemzamio'.

The new *Zamioculcas* plant is a naturally-occurring branch mutation of an unnamed selection of *Zamioculcas zamiifolia*, not patented. The new *Zamioculcas* plant was discovered and selected by the Inventor on a single plant of the mutation parent selection within a population of plants of the mutation parent selection in a controlled greenhouse environment in De Kwakel, The Netherlands on Jul. 10, 2012.

Asexual reproduction of the new *Zamioculcas* plant by vegetative cuttings in a controlled environment in De Kwakel, The Netherlands since July, 2012 has shown that the unique features of this new *Zamioculcas* plant are stable and reproduced true to type in successive generations of asexual reproduction.

SUMMARY OF THE INVENTION

Plants of the new *Zamioculcas* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Heemzamio'. These characteristics in combination distinguish 'Heemzamio' as a new and distinct *Zamioculcas* plant:

1. Upright plant habit with upwardly pointing pinnately-compound leaves.
2. Basally clumping habit.
3. Moderately vigorous growth habit.

4. Glossy leaflets that are dark greyed green and purple in color and at a distance, appear almost black in color.
5. Glossy and cylindrical leaf rachises that are dark greyed green in color.

Plants of the new *Zamioculcas* differ from plants of the mutation parent selection in the following characteristics:

1. Plants of the new *Zamioculcas* and the mutation parent selection differ in leaflet color as plants of the mutation parent selection have medium green-colored leaflets.
2. Plants of the new *Zamioculcas* and the mutation parent selection differ in leaf rachis color as plants of the mutation parent selection have medium green-colored leaf rachises.

Plants of the new *Zamioculcas* can also be compared to plants of *Zamioculcas zamiifolia* 'Lucky', disclosed in U.S. Plant Pat. No. 23,594. In side-by-side comparisons conducted in De Kwakel, The Netherlands, plants of the new *Zamioculcas* differed from plants of 'Lucky' in the following characteristics:

1. Plants of the new *Zamioculcas* were smaller than plants of 'Lucky'.
2. Plants of the new *Zamioculcas* and 'Lucky' differed in leaflet color as plants of 'Lucky' had medium green-colored leaflets.
3. Leaflet apices of plants of the new *Zamioculcas* were acute whereas leaflet apices of plants of 'Lucky' were rounded.
4. Plants of the new *Zamioculcas* and 'Lucky' differed in leaf rachis color as plants of 'Lucky' had medium green-colored leaf rachises.

BRIEF DESCRIPTION OF THE PHOTOGRAPH

The accompanying photograph illustrates the overall appearance of the new *Zamioculcas* showing the colors as true as it is reasonably possible to obtain in colored reproductions of this type. Colors in the photograph may differ slightly from the color values cited in the detailed botanical description which accurately describe the colors of the new *Zamioculcas* plant.

The photograph is a side perspective view of a typical plant of 'Heemzamio' grown in a container.

DETAILED BOTANICAL DESCRIPTION

The aforementioned photographs and following observations and measurements describe plants grown during the winter in 21-cm containers in a glass-covered greenhouse in De Kwakel, The Netherlands and under cultural practices typical of commercial *Zamioculcas* production. During the production of the plants, day temperatures ranged from 20° C. to 30° C. and night temperatures ranged from 18° C. to 26° C. Plants were 13 months from planting rooted plants when the photograph and the detailed description were taken. In the following description, color references are made to The Royal Horticultural Society Colour Chart, 1995 Edition, except where general terms of ordinary dictionary significance are used.

Botanical classification: *Zamioculcas zamiifolia* 'Heemzamio'.

Parentage: Naturally-occurring branch mutation of an unnamed selection of *Zamioculcas zamiifolia*, not patented.

Propagation:

*Type*.—By vegetative cuttings.

*Time to initiate roots, summer*.—About 21 days at temperatures about 20° C.

*Time to initiate roots, winter*.—About 30 days at temperatures about 20° C.

*Time to produce a rooted young plant, summer*.—About 140 days at temperatures about 20° C.

*Time to produce a rooted young plant, winter*.—About 200 days at temperatures about 20° C.

*Root description*.—Medium in thickness, fleshy; brownish white in color.

*Rooting habit*.—Freely branching, dense.

Plant description:

*Plant and growth habit*.—Upright plant habit with upwardly pointing leaves; stemless; pinnately compound leaves developing in basal clumps; typically about three to four leaves develop per clump; moderately vigorous growth habit.

*Plant height*.—About 30 cm.

*Plant diameter*.—About 15 cm to 20 cm.

Leaf Description:

*Leaf arrangement*.—Pinnately compound leaves with about 8 to 16 leaflets per leaf; leaflets sessile.

*Leaf length*.—About 20 cm.

*Leaf width*.—About 8 cm to 10 cm.

*Leaflet length*.—About 8 cm to 10 cm.

*Leaflet width*.—About 3.5 cm.

*Leaflet shape*.—Ovate.

*Leaflet apex*.—Acute.

*Leaflet base*.—Attenuate.

*Leaflet margin*.—Entire.

*Leaflet venation*.—Pinnate.

*Leaflet aspect*.—About 45° from vertical.

*Leaflet texture, upper and lower surfaces*.—Smooth, glabrous; thick.

*Leaflet luster, upper and lower surfaces*.—Glossy.

*Leaflet color*.—Developing leaflets, upper surface: Close to 146A; venation and margins, close to 200B. Developing leaflets, lower surface: Close to 146A; venation and margins, close to 187A Fully expanded leaflets, upper surface: Close to 189A; venation and margins, close to 187A to 187B. Fully expanded leaflets, lower surface: Close to 187B; venation and margins, close to 187B.

*Leaf rachises*.—Length (soil level to uppermost leaflet): About 24 cm. Length (soil level to lowermost leaflet): About 10 cm. Diameter (at the soil level): About 2 cm. Diameter (just below lowermost leaflet): About 1 cm. Diameter (at uppermost leaflet): About 4 mm. Shape: Cylindrical. Aspect: Mostly upright. Texture: Smooth, glabrous. Luster: Glossy. Color: Close to 197A.

Inflorescence description: Flower initiation and development has not been observed on plants of the new *Zamioculcas*.

Disease & pest resistance: Plants of the new *Zamioculcas* have not been observed to be resistant to pathogens or pests common to *Zamioculcas* plants.

Temperature tolerance: Plants of the new *Zamioculcas* have been observed to be tolerant to temperatures ranging from about 18° C. to about 38° C.

It is claimed:

1. A new and distinct *Zamioculcas* plant named 'Heemzamio' as illustrated and described.

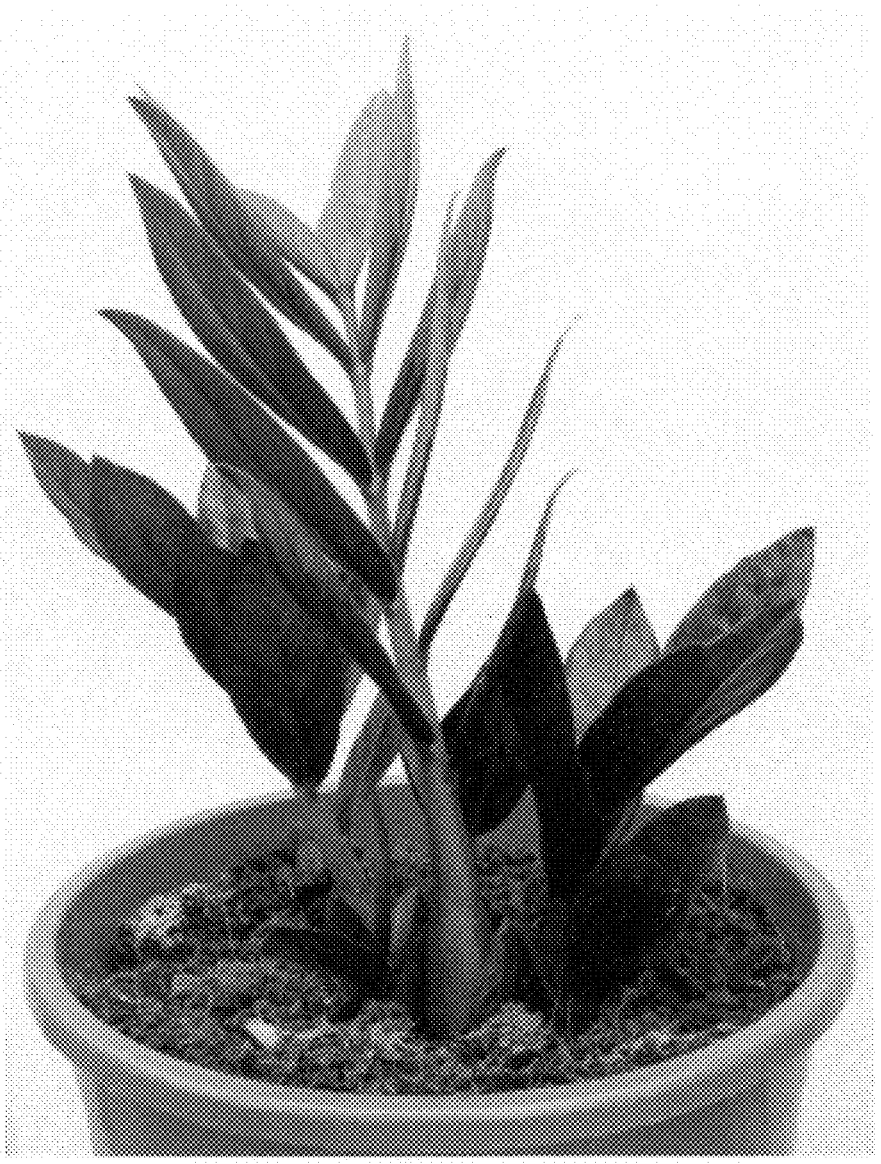

* * * * *